(12) United States Patent
McCormick et al.

(10) Patent No.: US 11,253,669 B2
(45) Date of Patent: Feb. 22, 2022

(54) ANESTHESIA BREATHING SYSTEM AND A METHOD AND KIT FOR DRYING AN ANESTHESIA BREATHING SYSTEM

(71) Applicant: GE Precision Healthcare LLC, Wauwatosa, WI (US)

(72) Inventors: Timothy P. McCormick, Madison, WI (US); James N. Mashak, Sun Prairie, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 323 days.

(21) Appl. No.: 16/404,907

(22) Filed: May 7, 2019

(65) Prior Publication Data

US 2020/0353200 A1 Nov. 12, 2020

(51) Int. Cl.
*A61M 16/10* (2006.01)
*A61M 16/22* (2006.01)
*A61M 16/00* (2006.01)

(52) U.S. Cl.
CPC .......... *A61M 16/104* (2013.01); *A61M 16/22* (2013.01); *A61M 16/0096* (2013.01)

(58) Field of Classification Search
CPC .......... A61M 16/0075; A61M 16/0078; A61M 16/0081; A61M 16/0084; A61M 16/0875; A61M 16/0883; A61M 16/0891; A61M 16/01; A61M 16/104; A61M 16/009; A61M 16/204; A61M 16/205; A61M 16/22
USPC ................... 34/413, 437, 439, 443
See application file for complete search history.

(56) References Cited

U.S. PATENT DOCUMENTS

| | | | | |
|---|---|---|---|---|
| 4,354,514 A | * | 10/1982 | Sundheimer | A61B 90/70 134/102.3 |
| 5,673,688 A | * | 10/1997 | Tham | A61M 16/104 128/204.22 |
| 6,523,538 B1 | * | 2/2003 | Wikefeldt | A61M 16/01 128/204.18 |
| 6,619,289 B1 | * | 9/2003 | Mashak | A61M 16/0808 128/205.12 |

(Continued)

OTHER PUBLICATIONS

Drager, No More and No Less Than Necessary—Perseus A500 for Accurate Dosage and Simplified Workflows, Background text: Perseus A500, Dragerwerk AG & Co. KGaA.

(Continued)

*Primary Examiner* — Colin W Stuart
*Assistant Examiner* — Douglas Y Sul
(74) *Attorney, Agent, or Firm* — Andrus Intellectual Property Law, LLP

(57) ABSTRACT

A method of drying an anesthesia breathing system includes removing a $CO_2$ absorber from the anesthesia breathing system, when the $CO_2$ absorber is connected to an absorber inlet port and an absorber outlet port. The method further includes moving a bag-to-vent flow diverter to an intermediate position so as to simultaneously open both a bag channel and a ventilator channel, and connecting an inspiratory port and an expiratory port of the anesthesia breathing system together. A dry gas source is connected to an absorber outlet channel, and then a dry gas flow is provided through the bag channel and the ventilator channel so as to dry out moisture from a bag circuit and a ventilator circuit of the anesthesia breathing system.

20 Claims, 5 Drawing Sheets

(56) References Cited

U.S. PATENT DOCUMENTS

| | | | | |
|---|---|---|---|---|
| 7,992,555 B2 * | 8/2011 | Heinonen | ............. | A61M 16/01 |
| | | | | 128/204.21 |
| 8,627,817 B2 | 1/2014 | Heesch | | |
| 2005/0257790 A1 * | 11/2005 | McNeirney | ......... | A61M 16/107 |
| | | | | 128/203.12 |
| 2007/0074727 A1 * | 4/2007 | Mills | ...................... | B01D 53/02 |
| | | | | 128/205.28 |
| 2011/0061650 A1 * | 3/2011 | Heesch | ............. | A61M 16/0833 |
| | | | | 128/203.12 |
| 2013/0102916 A1 * | 4/2013 | Colbaugh | ............ | A61B 5/4818 |
| | | | | 600/533 |

OTHER PUBLICATIONS

Drager, Technology Insights for low- and minimial-flow anaesthesia, Dragerwerk AG & Co. KGaA.

* cited by examiner

ANESTHESIA BREATHING SYSTEM AND A METHOD AND KIT FOR DRYING AN ANESTHESIA BREATHING SYSTEM

BACKGROUND

The present disclosure generally relates to anesthesia breathing systems, and more particularly to methods and systems for drying anesthesia breathing systems and kits for drying anesthesia breathing systems.

Conventional anesthesia breathing systems have a patient delivery circuit comprising an inspiratory section and an expiratory section. The patient delivery circuit delivers breathing gases to the patient comprising oxygen and other gases, optionally infused with an inhalational anesthetic agent. As used herein, the term "ventilation" refers to a process of providing mechanical assistance to a patient for breathing. As used herein, "breathing gases" refer to gases inhaled by the patient from the patient delivery circuit and gases exhaled by the patient into the patient delivery circuit during breathing. Also, as used herein, "inspiratory gases" refers to gases transported along an inspiratory section of the patient delivery circuit, including gases that are inhaled or inspired by a patient from the inspiratory section of the patient delivery circuit and gases bypassing patient inhalation and transported directly into the expiratory section of the patient delivery circuit. Also, as used herein, "expiratory gases" refer to gases that are exhaled or expired by the patient into the expiratory section of the patient delivery circuit and gases bypassing inhalation and transported directly into the expiratory section from the inspiratory section which are not exhaled by the patient, both of which are transported along the expiratory section. Conventional anesthesia delivery systems are typically configured as bellows systems where patient ventilation is driven by a bellow.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a method of drying an anesthesia breathing system includes removing a $CO_2$ absorber from the anesthesia breathing system, when the $CO_2$ absorber is connected to an absorber inlet port and an absorber outlet port. The method further includes moving a bag-to-vent flow diverter to an intermediate position so as to simultaneously open both a bag channel and a ventilator channel, and connecting an inspiratory port and an expiratory port of the anesthesia breathing system together. A dry gas source is connected to an absorber outlet channel, and then a dry gas flow is provided through the bag channel and the ventilator channel so as to dry out moisture from a bag circuit and a ventilator circuit of the anesthesia breathing system.

In an embodiment of an anesthesia breathing system, a $CO_2$ absorber is connectable to an absorber inlet channel and an absorber outlet channel, a bag circuit where gas flow is driven by a bag, and a ventilator circuit where gas flow is driven by a bellows. The system further includes a flow diverter controllable to simultaneously open both the bag circuit and the ventilator circuit, and an inspiratory channel configured to transport inspiratory gases and an expiratory channel configured to transport expiratory gases from a patient. This system further includes a dry gas source. The dry gas source is connectable to the absorber outlet channel. A controller is configured to receive a user input to activate a drying mode. The controller is further configured to control a dry gas flow from a dry gas source through the bag circuit and the ventilator circuit so as to dry out moisture therefrom.

A kit for drying an anesthesia breathing system includes a switch retainer configured to be placed on a manually operable bag-to-vent switch lever of an anesthesia breathing system, wherein the switch retainer is configured to hold the bag-to-vent switch lever in an intermediate position between a bag position that closes the ventilator circuit and a ventilator position that closes the bag circuit. The kit further includes a dry gas input tube configured to connect an absorber outlet port of the anesthesia breathing system to a dry gas source such that dry gas flows through the ventilator channel and the bag channel simultaneously. The dry gas input tube may have a $CO_2$ outlet fitting on one end that is configured to connect to the absorber outlet port when a $CO_2$ absorber is removed from the anesthesia breathing system, and a dry gas source fitting on an opposite end that is configured to connect to the dry gas source.

Various other features, objects, and advantages of the invention will be made apparent from the following description taken together with the drawings.

BRIEF DESCRIPTION OF THE DRAWINGS

The present disclosure is described with reference to the following Figures.

FIG. 2 is a system diagram illustrating a breathing system in a drying mode showing a flow path of drying gas there through.

DETAILED DESCRIPTION

Figure 1:
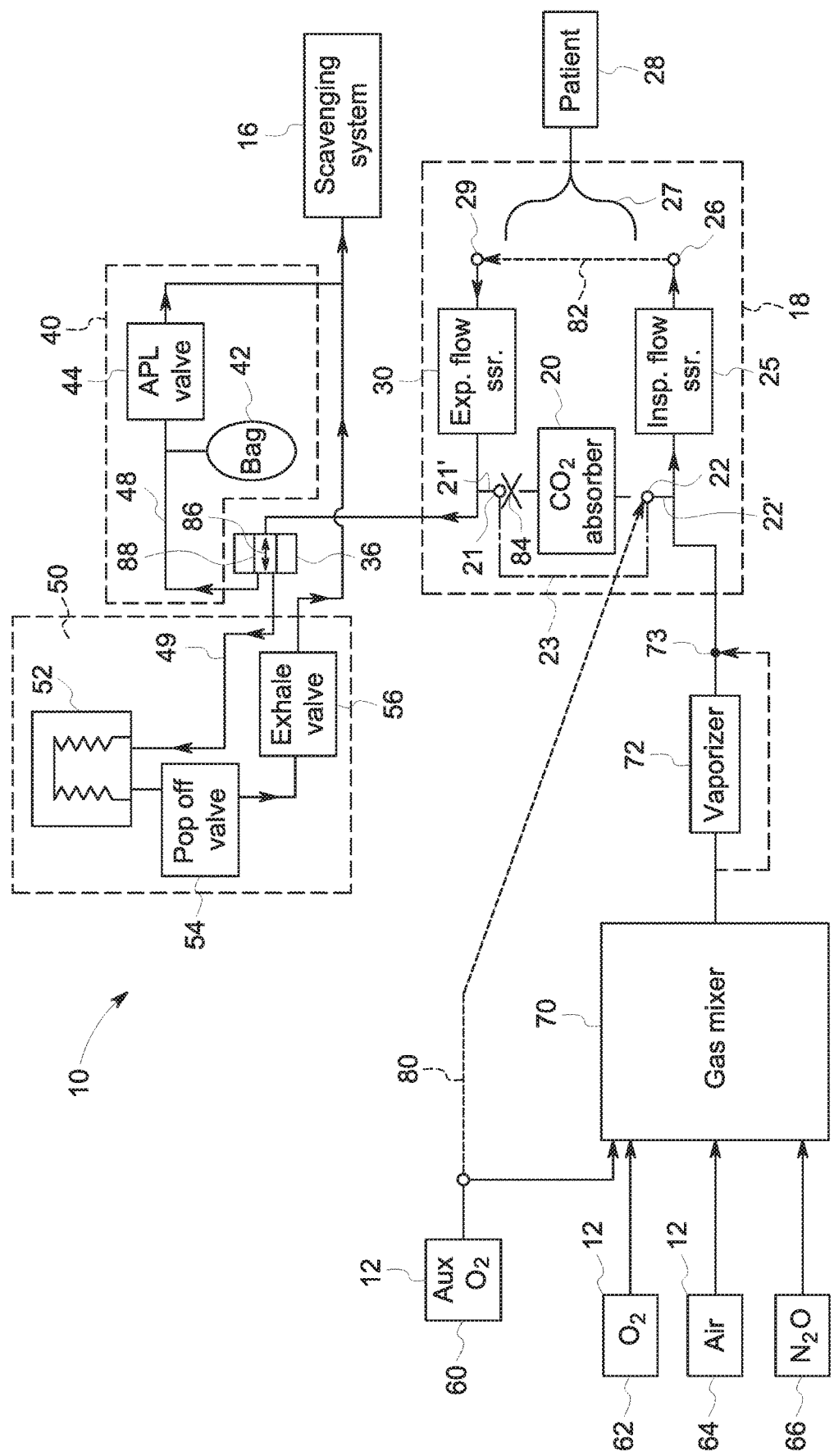
FIG. 1 illustrates an exemplary breathing system in a drying mode and utilizing a method of drying an anesthesia breathing system.

The inventors have recognized a problem with existing breathing systems where mold growth occurs within the gas flow path that reaches the patient. Water vapor accumulates within breathing systems during patient ventilation delivery. For example, water vapor is produced as a result of a chemical reaction in the $CO_2$ absorber, which may collect in an inspiratory section of the breathing circuit, such as between an outlet of the $CO_2$ absorber and an inspiratory port that delivers inspiratory gases when the system 10 is operational to ventilate a patient. The water vapor may also collect in other areas of the breathing system, such as in a ventilator circuit having a bellows or in a bag circuit having a manual bag and APL valve. This moisture can lead to mold growth. Thus, the inventors have recognized that a practical method and system are needed to enable thorough drying of the breathing system of an anesthesia machine in order to reduce the likelihood of mold growth therein. An efficient way of drying a breathing system does not exist today. While some systems use fresh gas at high flow rates to dry out certain areas of an anesthesia machine, such systems do not efficiently dry all compartments of a breathing system because multiple dead-end flow paths exist in typical breathing system configurations and the drying gas is not circulated through the entire breathing system.

In one embodiment, a dry gas source is connected at an outlet port of the $CO_2$ absorber and a bag-to-vent flow diverter is placed in an intermediate position so as to open both the bag channel and the ventilator channel so that both paths can be dried out. In one embodiment, a kit for drying an anesthesia breathing system is provided including elements attachable to the breathing system in order to facilitate drying. In one embodiment, the kit includes a switch retainer configured to place a manually-operable bag-to-vent switch lever in an intermediate position so as to open both the bag channel and the ventilator channel, and a dry gas input tube configured to connect the $CO_2$ absorber outlet port to a dry gas supply such that the dry gas can flow through both the ventilator channel and the bag channel simultaneously. The kit may further include a short circuit connection tube configured to connect an inspiratory port to an expiratory port of the anesthesia breathing system. In another embodiment, the anesthesia breathing system may include a controller configured to receive a user input to activate a drying mode. The controller may be configured to control one or more valves to open channels within the breathing system to connect the dry gas to the inspiratory section, a bag portion, and a ventilator portion of the anesthesia breathing system so that all gas channels can be thoroughly dried out. For example, the anesthesia breathing system may be dried out between patient cases or during long periods of nonuse, such as overnight, so as to prevent mold growth and allow more effective cleaning and sterilization of the entirety of the gas path in the breathing system.

FIG. 1 depicts one embodiment of an anesthesia breathing system 10 that includes a gas mixer 70, a patient delivery circuit 18, a bag circuit 40, and a ventilator circuit 50. During patient ventilation, input gas would also flow from a gas mixer 70 that mixes several gas sources, such as the main $O_2$ source 62, a medical air source 64, and/or a nitrous oxide ($N_2O$) source 66. In the example, the output of the gas mixer 70 is provided to the vaporizer 72 that provides vaporized anesthetic agent into the gas to be delivered to the patient. In certain embodiments, a bypass channel may also be provided that allows gases to bypass the vaporizer on the path to the patient 28. In certain embodiments, fresh gas may also be insertable into the system 10 at the bypass port 73 between the gas mixer 70 and the inspiratory port 26. Gas flows through the inspiratory section of the patient delivery circuit 18, including through the inspiratory flow sensor 25, the inspiratory port 26, and to a connected patient-end connector 27. The patient-end connector 27 may be, for example, a wye tube that connects to a patient interface, such as a mask or endotracheal tube, in order to deliver and receive breathing gases for the patient 28. During use, the expiratory gases from the patient 28 travel through the patient connector 27 to the expiratory port 29 and past the expiratory flow sensor 30.

A bag-to-vent flow diverter 36 is positioned to divert gas to one of the bag circuit 40, where ventilation is driven by the manual bag 42, and the ventilator circuit 50, where ventilation is driven by expansion and compression of the bellows 52. Ordinarily, the bag-to-vent flow diverter occupies either of two positions such that gas flow is directed into either a bag channel 48 or a ventilator channel 49, but not both. Thus, during patient ventilation, the bag-to-vent flow diverter opens only one drive channel at a time and does not permit both the bag channel 48 and the ventilator channel 49 to be opened simultaneously. This is a safety feature because it would be dangerous for the patient if both channels were opened simultaneously during ventilation delivery. For example, the bag-to-vent flow diverter may be controlled by a bag-to-vent switch lever 37 (see FIG. 3) movable by a clinician operating the system 10. The lever 37 may be configured to only stay in one of either a bag position that opens the bag channel 48 and closes the ventilator channel 49 and a ventilator position that opens the ventilator channel 49 and closes the bag channel 48. Such a manually operable bag-to-vent switch is a common bag-to-vent flow diverter mechanism in the relevant art.

In the bag position, the bag-to-vent flow diverter 36 directs gas into the bag channel 48 where patient ventilation is driven by a bag 42 operating in conjunction with an APL valve 44 to control patient ventilation. In the vent position, the bag-to-vent flow diverter 36 directs gas into the ventilation channel 49 where it passes through the bellows 52, the popup valve 54, and the exhalation valve 56. During normal operation, these and other elements in the bag circuit 40 and the ventilator circuit 50, as well as in the patient delivery circuit 18, may get a buildup of moisture. Over time, this can become problematic as it can lead to mold growth or other types of contamination. Thus, the inventors have devised a way for dry gas to be circulated throughout the breathing system 10 in order to dry out the entire gas path.

FIG. 1 depicts a gas path in an exemplary breathing system 10, where dry gas from a dry gas source 12, in this case an auxiliary $O_2$ source 60, is connected to a $CO_2$ absorber outlet 22 and flows throughout the various circuits 18, 40, 50 along the depicted path. The gas flows to a scavenging system 16 that removes anesthetic agent or contaminants carried out by the drying gas. The dry gas does not flow through the $CO_2$ absorber 20, which is the one area of the system 10 that should not be dried.

Breathing systems 10 typically have removable $CO_2$ absorbers 20. $CO_2$ absorbers are often canisters that can be removed and replaced on the system 10, as needed. The $CO_2$ absorber connects into the gas path at a $CO_2$ absorber inlet 21, where exhalation gases flow into the $CO_2$ absorber. The $CO_2$ gets removed from the exhalation gases, and the remaining gases exit the $CO_2$ absorber and flow back into the gas path through the absorber exit port 22 with much of the $CO_2$ removed. In certain embodiments, a $CO_2$ channel 23 may be provided, wherein removal of the $CO_2$ absorber 20 causes the $CO_2$ bypass channel 23 to open. Valves may be provided in each of the absorber inlet port 21 and the absorber outlet port 22, wherein the valves are configured to close the ports off to atmosphere and open the $CO_2$ bypass channel 23 upon removal of the absorber.

As disclosed herein, the drying occurs by connecting one or more of the available dry gas sources, such as the auxiliary $O_2$ source 60, the main $O_2$ source 62 (such as a well gas supply), or a medical air source 64 (such as a wall supply). The dry gas from one or more of these sources is directed through the inspiratory section of the patient delivery circuit 18, bypassing the $CO_2$ absorber 20, which may be removed during drying. In one embodiment, the $CO_2$ absorber is removed from the breathing system 10 and the dry gas source 12 is connected to the $CO_2$ absorber outlet 22, and thereby dries the outlet and the remainder of the inspiratory section. In certain embodiments, a fresh gas source may also be activated to provide a fresh gas flow through an inlet port 73 during the cleaning period. By providing at least some fresh gas flow through the inlet port 73 during the drying process, the backflow of the contaminated drying gas into the fresh gas input line can be prevented.

Figure 2:
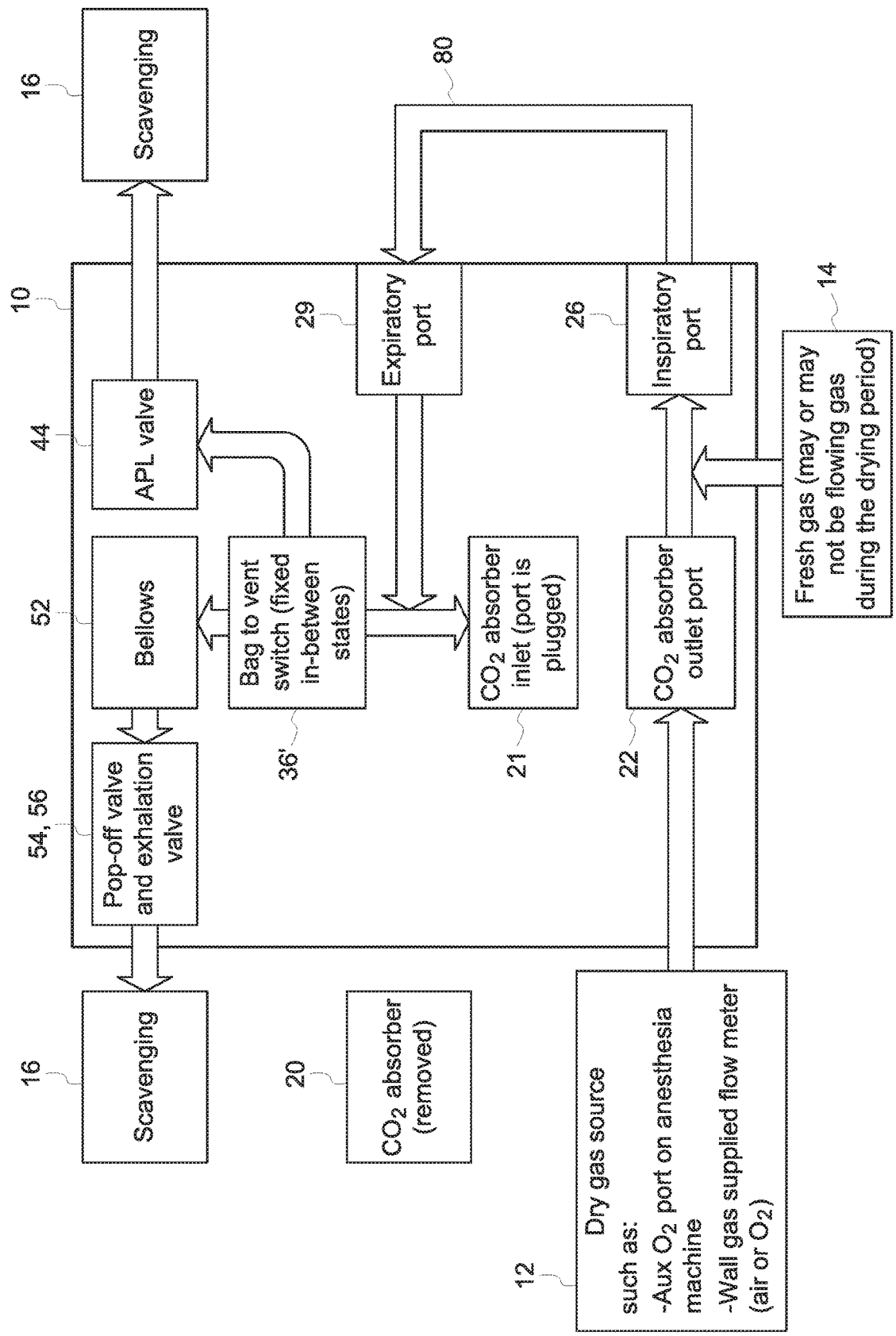

FIG. 1 depicts a desired gas path for the drying method. FIG. 2 also exemplifies a gas path for a method of drying an anesthesia breathing system 10. The inspiratory section and the expiratory section of the patient delivery circuit 18 are connected together by a short circuit connection 82. The connection 82 short circuits the patient-end of the patient delivery circuit—i.e., cutting out the patient 28 end. For example, a tube or other connection may be provided between the inspiratory port 26 and expiratory port 29. Alternatively, the short circuit connection 82 may be a wye tube with the why occluded. In other embodiments, the short circuit may happen at another location inside the system 10 that connects the inspiratory section with the expiratory section.

The dry gas from the dry gas source 12 is then provided to the expiratory section, flowing past the expiratory flow sensor 30 and past the $CO_2$ absorber inlet 21. Thus, the $CO_2$ absorber inlet 21 must be plugged or otherwise blocked in order to force the drying gas to continue along the depicted path. In embodiments having a $CO_2$ bypass channel 23, the bypass channel must be blocked. The drying gas flows to the flow diverter 36 may be a bag-to-vent switch or other diverter controllable to divert flow between the bag channel 48 and the vent channel 49. The bag-to-vent flow diverter may be controllable to simultaneously open both the bag channel 48 and the ventilator channel 49. For example, the flow diverter 36 is moved into an intermediate position 86 that simultaneously opens both the bag channel 48 and the ventilator channel 49 so that gas can flow in both directions out of the diverter 36. In one embodiment, the flow diverter 36 is a bag-to-vent switch with a manually operable lever 37 (FIG. 3).

In other embodiments, the flow diverter 36 operable in the drying mode may bypass the bag-to-vent switch and configured to divert the dry gas flow into both of the bag channel 48 and the ventilator channel 49 so that gas flows though both of the respective circuits 40, 50. The gas flows in the bag circuit 40, including through the APL valve 44, and out toward the scavenging system 16. The dry gas also flows through the ventilator circuit 50, including through the bellows 52, the popup valve 54, and the exhalation valve 56, and then out to the scavenging system 16.

Figure 3:
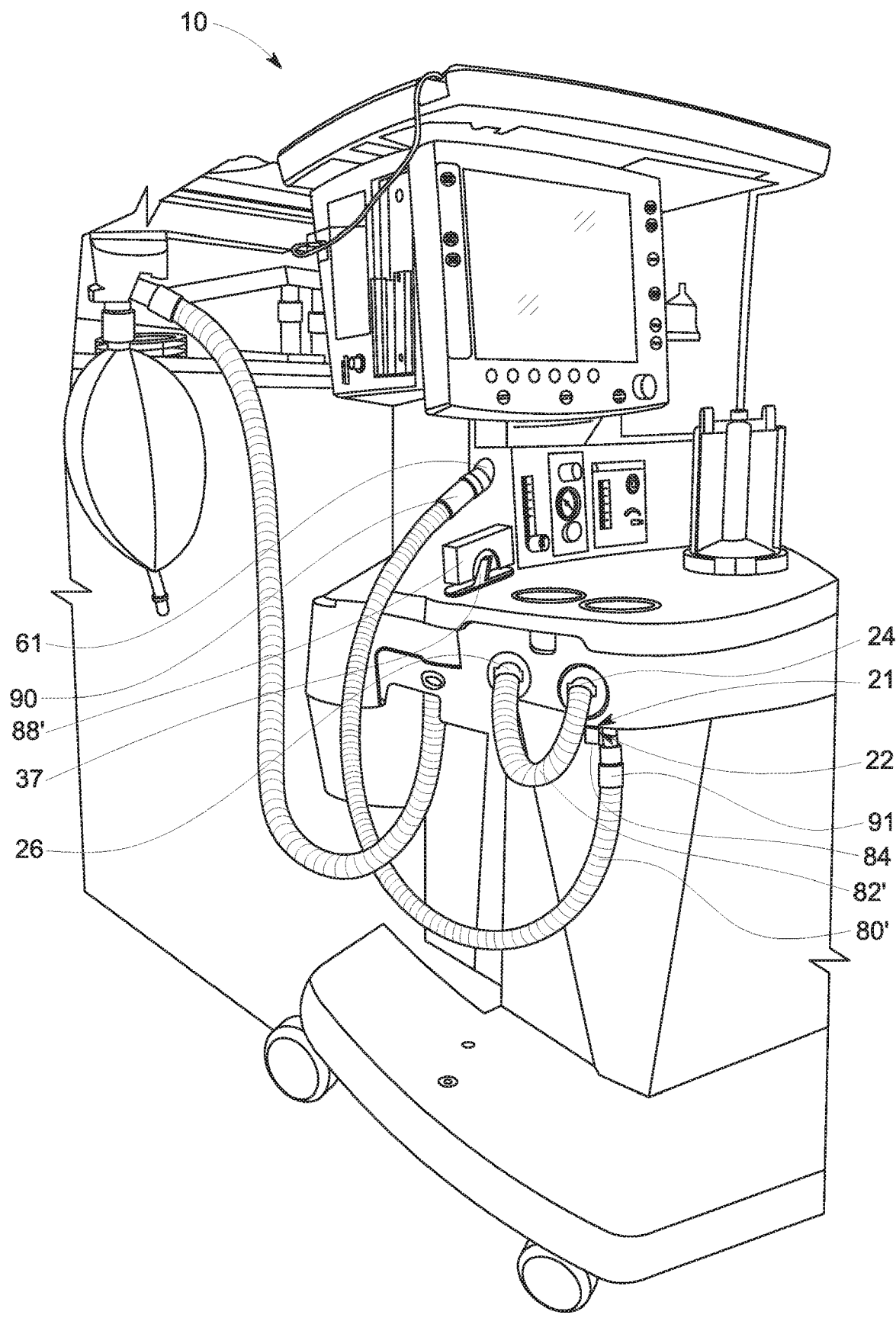
FIG. 3 depicts an embodiment of a breathing system with a drying kit attached thereto.

FIG. 3 is an exterior view of an exemplary breathing system 10 operating in a cleaning mode. Several elements are attached to the breathing system 10. A short circuit connection tube 82' is connected between the inspiratory port 26 and the expiratory port 29. The short circuit connection tube 82' may include a fitting on each end for connecting to the respective ports 26, 29. A switch retainer 88' is connected to the bag-to-vent switch lever 37 in order to hold the lever in an intermediate position, which in turn forces the flow diverter 36 into the intermediate position 86. For example, the switch retainer 88 may be a clip that sits over the switch lever 37 and holds the lever between the bag position and the vent position. In other embodiments, the switch retainer 88 may be a spacer or other device inserted onto one or both sides of the switch lever 37 in order to push the switch lever 37 into a middle position where both channels 48 and 49 are opened simultaneously.

A dry gas input connector in the form of a tube 80' connects between the auxiliary $O_2$ port 61 and the $CO_2$ absorber outlet 22. In other embodiments, the dry gas input connector 80 may be a tube configured to connect between a wall gas supply outlet in order to connect a wall gas supply, such as $O_2$ or medical air, to the outlet port 22 in order to supply dry gas. The dry gas input tube 80' has a first end with a dry gas supply fitting 90 that connects to the dry gas port.

In the depicted embodiment, the dry gas supply fitting 90 is configured to connect to the auxiliary $O_2$ port 61 of the breathing system 10. In other embodiments, the dry gas supply fitting 90 may be configured to connect to a different type of port, depending on the intended dry gas supply. The dry gas input tube 80' has a second end, opposite the first end, with a $CO_2$ outlet fitting 91 configured to connect to the $CO_2$ outlet port 22 when the $CO_2$ absorber 20 canister is removed. For example, the $CO_2$ outlet fitting 91 and/or the dry gas supply fitting 90 may be a barb fitting end that is configured to connect to the respective port.

In certain embodiments, an absorber inlet plug 84 is also provided that plugs or otherwise blocks the absorber inlet port 21 when the $CO_2$ absorber 20 is removed. In embodiments having a $CO_2$ bypass channel 23, the absorber inlet plug 84 is configured to plug the inlet port 21 while also closing off the bypass channel 23. For example, the $CO_2$ absorber inlet plug 84 may be a plastic fitting or rubber stopper configured to fit over or otherwise occlude the absorber inlet port 21. In certain embodiments, the absorber inlet plug 84 is connected to the $CO_2$ outlet fitting 91 such that the plug is attached to and supplied with the dry gas input tube 80'. For example, a unified fitting may be provided that mimics the connection end of the $CO_2$ absorber, the unified fitting having an element or portion that occludes the inlet port 21 and facilitates connection between the dry gas input tube 80' and the absorber outlet port 22.

The breathing system 10 may be any available breathing system, and the inventors have recognized that currently available breathing systems can by dried out by arranging the system as disclosed, e.g., by attaching the above-disclosed elements thereto. In certain embodiments, one or more of the devices depicted in FIG. 3 are provided together as a kit for drying the breathing system 10. In one embodiment, the kit includes the switch retainer 88, such as clip 88', and the dry gas input tube 80'. In other embodiments, the kit for drying the anesthesia breathing system 10 further includes the absorber inlet plug 84. In one embodiment, the absorber inlet plug 84 may be connected to the $CO_2$ outlet fitting 91, such as by a tether or being a unified fitting as described above. Alternatively or additionally, the kit may include the short circuit connection tube 82' for connection between the inspiratory port 26 and the expiratory port 29.

In still another embodiment, both the inlet and the outlet ports 21 and 22 for the $CO_2$ absorber may be plugged, as described above, and the gas mixer 70 may be utilized as the dry gas source to dry out the breathing system, including the patient delivery circuit 18, the bag circuit 40, and the ventilator circuit 50. In such an embodiment, the kit may include the switch retainer 88 and a plug or set of plugs that closes off both ports 21 and 22 for the $CO_2$ absorber. The dry gas source 70 can then be activated in a "drying mode" to circulate the drying gas.

Figure 4:
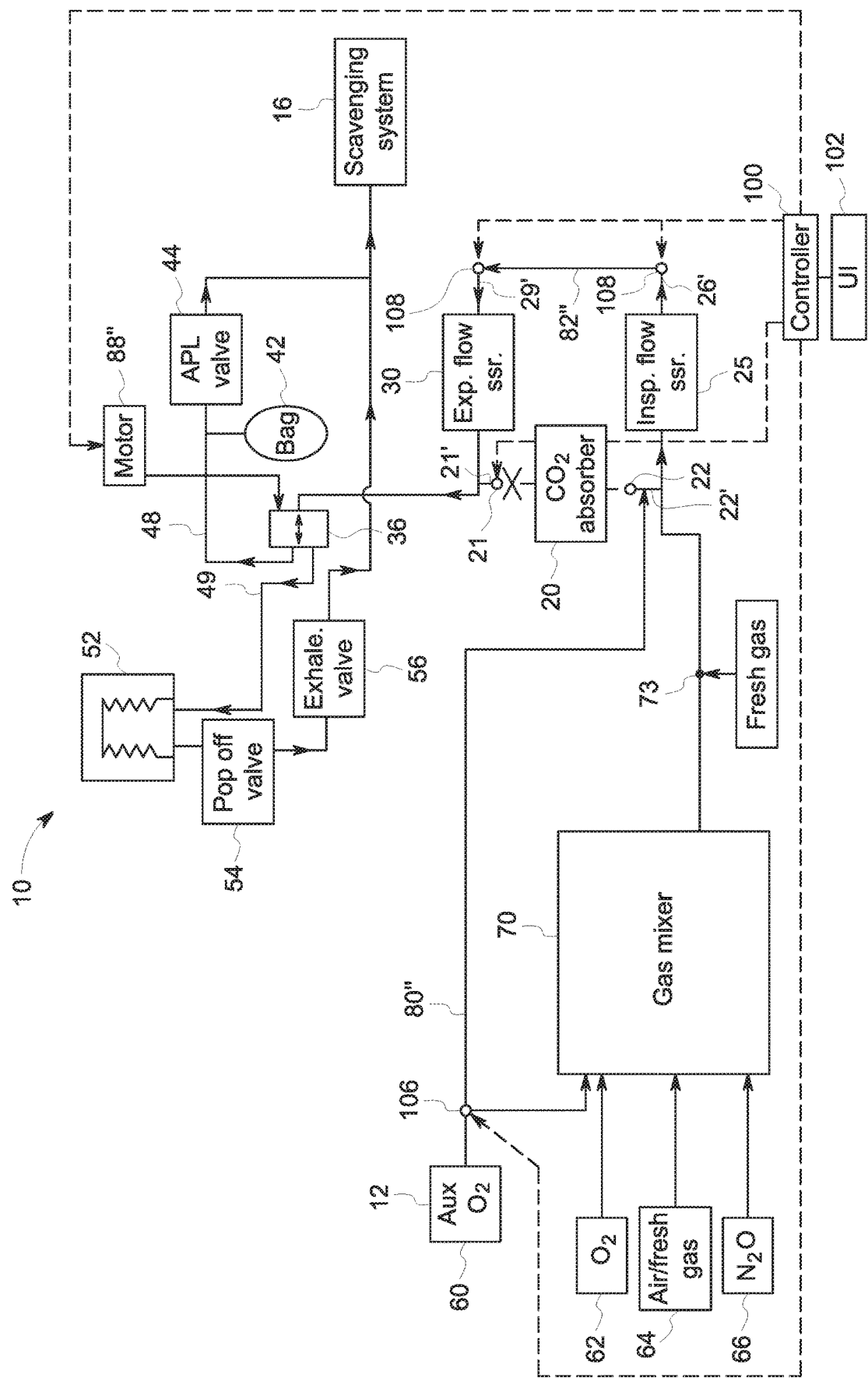
FIG. 4 depicts another embodiment of a breathing system configured to automatically activate a drying mode based on a user input.

FIG. 4 depicts another embodiment of a breathing system 10 that executes the disclosed drying method. In certain embodiments, the system 10 may further include a user interface 102 that receives user inputs, such as a digital user interface or a manual user interface by which a user can switch the system 10 into a drying mode. On a digital user interface 102, a menu may be provided whereby, when the breathing system 10 is not in a therapy state delivering breathing gases to a patient, a menu may allow a user to select a drying mode. In certain embodiments, the controller 100, such as in conjunction with the user interface 102, may instruct a user to remove the $CO_2$ absorber 20 from the breathing system 10 prior to activating the drying mode.

The system of FIG. 4 is configured to automatically execute the drying method wherein a controller 100 controls one or more switches and/or valves within the system in order to connect a dry gas source and circulate gas through the patient delivery circuit 18, the bag circuit 40, and the ventilator circuit 50 (see FIG. 1 for the circuit labels, which have been removed from FIG. 4 for visual clarity). The controller 100 may control, for example, a valve 106 to connect the dry gas source 12, such as the auxiliary $O_2$ 60, to the drying circuit. For example, the breathing system 10 may be internally plumbed to provide a dry gas input connector 80" that internally connects the auxiliary $O_2$ 60 or other dry gas source to the absorber inlet channel 22'. In one embodiment, the absorber inlet port 22 has a valve that automatically closes when the $CO_2$ absorber 20 is removed. The controller 100 controls the valve 106 to provide the $O_2$ from the auxiliary $O_2$ 60 into the absorber outlet channel 22'. As long as the $CO_2$ absorber 20 is removed, the absorber outlet port 22 is closed by the valve, and thus the dry gas is forced into the inspiratory channel 26.

In the drying mode, the controller 100 may be configured to further control one or more valves 108 to connect the inspiratory channel to the expiratory channel. In the depicted example at FIG. 4, the system 10 may be plumbed with a short circuit connection 82' that connects the inspiratory channel 26' to the expiratory channel 29'. The valves 108 automatically open, via the controller 100, in the drying mode so as to short circuit the two sections of the patient delivery circuit 18. The controller may also be configured to automatically control dry gas flow from the dry gas supply, such as to control the auxiliary $O_2$ supply 60 to turn it on, such as to provide a relatively low flow. In one example, the controller 100 controls flow from the auxiliary $O_2$ 60 to supply about six liters per minute of $O_2$ flow.

The controller 100 also controls the flow diverter 36, such as to place it in an intermediate position. For example, the controller 100 may control a switch retainer 88 that forces the bag-to-vent switch into a centered position. To provide just one example, the switch retainer 88 may be a stepper motor 88" or other electromechanical actuator that holds the switch 36 in the intermediate position. In another embodiment, the system may be internally plumbed to bypass the bag-to-vent switch so as to provide flow into both the bag circuit 40 and the ventilator circuit 50 during the drying mode only. In such an embodiment, the flow diverter may include one or more valves that may open to direct flow into the bag channel 48 and the ventilator channel 49 simultaneously, bypassing any bag-to-vent switch.

In an embodiment like that shown in FIG. 4, where the system 10 is internally configured to execute the drying method, the system 10 may be configured such that the user only needs to provide control input to enter the drying mode. In other embodiments, the user may also need to remove the $CO_2$ absorber 20 or otherwise disconnect the $CO_2$ absorber 20 from the $CO_2$ absorber outlet port 22.

Figure 5:
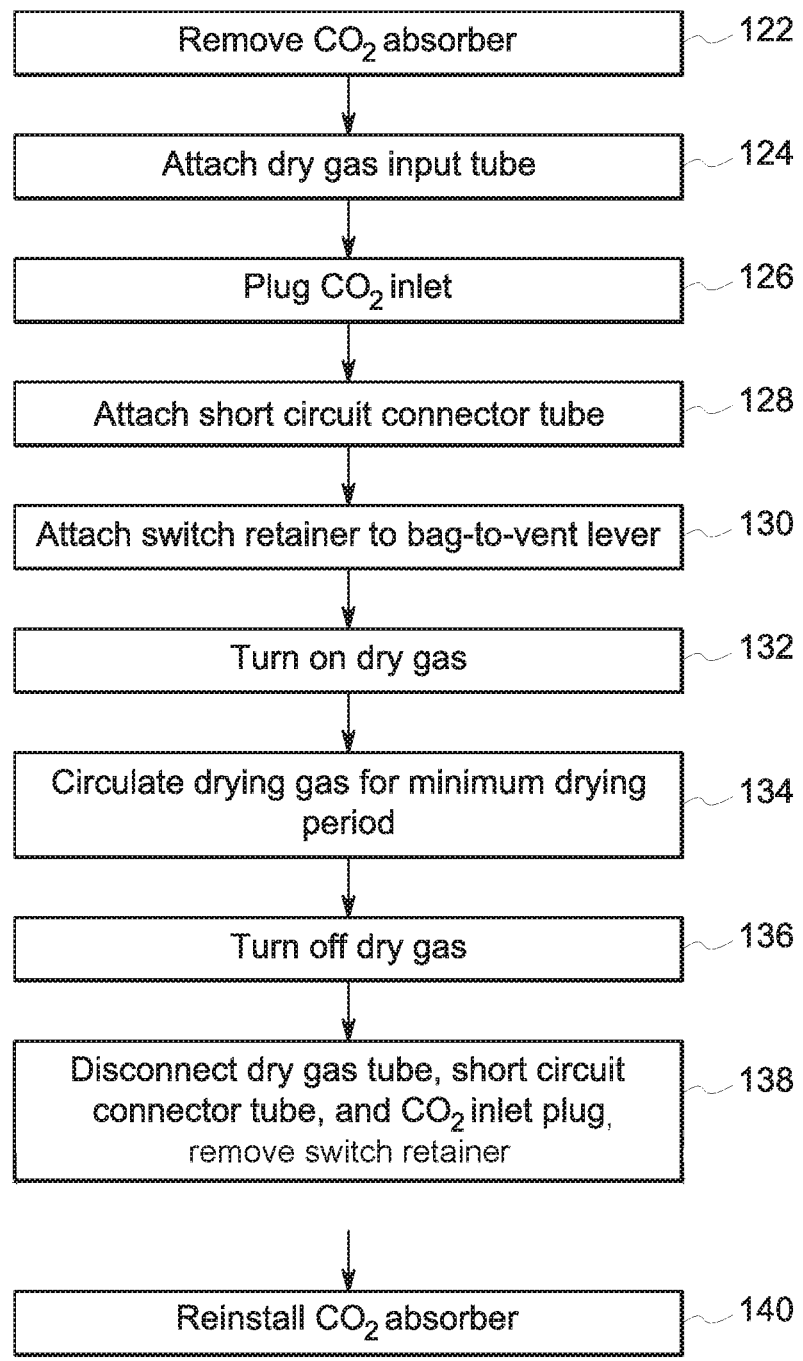
FIG. 5 depicts one embodiment of a method of drying a breathing system.

In embodiments like that depicted in FIG. 3 where a kit of parts are attached to the anesthesia breathing system 10, the drying method may include several steps performed by a user to facilitate drying of the system 10. FIG. 5 is a flow chart exemplifying method steps of one such embodiment. In the depicted method 120 of drying the anesthesia breathing system 10, the user removes the $CO_2$ absorber at step 122. The dry gas input tube 80' is attached at step 124 between the $CO_2$ outlet port 22 and the dry gas source 12. In certain embodiments, the $CO_2$ inlet 21 is plugged at step 126, such as by inserting the absorber inlet plug 84 over the absorber inlet port 21. In other embodiments, the absorber inlet port 21 may include a valve that automatically closes when the $CO_2$ absorber 20 removed, thereby automatically closing off the absorber inlet channel 21' and eliminating the need for a user to connect a plug. However, in systems having a $CO_2$ bypass channel 23, an absorber inlet plug may still be required in order to block off the bypass channel 23.

The inspiratory port 26 and the expiratory port 29 are then connected at step 128, such as with the short circuit connection tube 82'. In various embodiments, the short circuit connection tube may be a typical wye tube with the wye patient connector occluded, or may be a single tube as shown in FIG. 3. At step 130, the switch retainer 88' is connected to the bag-to-vent lever 37. As described above, the switch retainer 88' may be any device that connects to the bag-to-vent lever 37 and holds it in a centered, or intermediate, position between the bag position and the vent position. Thereby, both the bag circuit 40 and the vent circuit 50 are opened. In certain embodiments, the switch retainer 88' is configured to minimize the chance that the switch retainer 88' could be left on when the breathing system 10 is being operated to ventilate a patient 28. A person having ordinary skill in the art will understand that, in various embodiments, a user may perform one or more of steps 122 through 130 in a different order than that depicted at FIG. 5.

At step 132, the user turns on the auxiliary $O_2$ supply. For example, the auxiliary $O_2$ may be provided at a relatively low flow, such as at around six liters per minute. In various other examples, the $CO_2$ outlet may be connected to a different dry gas source than the auxiliary $O_2$, and in such an embodiment, the respective gas source will be likewise activated. The system will then be left to circulate the dry gas through the path depicted in the figures for at least a minimum drying period. A minimum drying period may be system-specific and represents a minimum amount of time needed to fully dry the various circuits 18, 40, 50 after an ordinary use case. For example, the minimum drying period may be one hour or may be several hours. In other embodiments, the system may require 12 hours of drying, such as drying overnight. After the drying period is over, the dry gas is turned off at step 136, the dry gas input tube and short circuit connector tubes are disconnected and the switch retainer is removed at step 138, and the $CO_2$ absorber is reinstalled at step 140.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:

1. A method of drying an anesthesia breathing system, the method comprising:
    removing a $CO_2$ absorber from the anesthesia breathing system, wherein the $CO_2$ absorber is connected to an absorber inlet port and an absorber outlet port of the anesthesia breathing system;

moving a bag-to-vent flow diverter to an intermediate position so as to simultaneously open both a bag channel and a ventilator channel;
connecting an inspiratory port of the anesthesia breathing system to an expiratory port of the anesthesia breathing system;
connecting a dry gas source to an absorber outlet channel;
inserting a plug into the absorber inlet port; and
providing a dry gas flow from the dry gas source through the bag channel and the ventilator channel so as to dry out moisture from a bag circuit and a ventilator circuit of the anesthesia breathing system.

2. The method of claim 1, wherein inserting the plug into the absorber inlet port closes a $CO_2$ bypass channel.

3. The method of claim 1, wherein the dry gas source is an auxiliary $O_2$ source of the anesthesia breathing system, and wherein connecting the dry gas source includes connecting one end of a tube to the absorber outlet port and an opposite end of the tube to an auxiliary $O_2$ outlet.

4. The method of claim 1, wherein the dry gas source is medical air or $O_2$ from a wall gas source, and wherein connecting the dry gas source includes connecting one end of a tube to the absorber outlet port and an opposite end of the tube to a wall gas outlet.

5. The method of claim 1, wherein moving the bag-to-vent flow diverter to an intermediate position includes placing a switch retainer on a manually operable bag-to-vent switch lever, wherein the switch retainer holds the bag-to-vent switch lever in an intermediate position between a bag position that closes the ventilator channel and a ventilator position that closes the bag channel.

6. The method of claim 1, wherein the anesthesia breathing system includes a valve controllable to connect the dry gas source to the absorber outlet port, and wherein connecting the dry gas source to the absorber outlet channel includes controlling the valve.

7. The method of claim 6, wherein moving the bag-to-vent flow diverter to an intermediate position includes controlling an electromechanical actuator to move the bag-to-vent flow diverter into the intermediate position.

8. The method of claim 1, further comprising providing a fresh gas flow through a gas inlet port of the anesthesia breathing system.

9. An anesthesia breathing system comprising:
a $CO_2$ absorber connectable to an absorber inlet channel and an absorber outlet channel;
a bag circuit where gas flow is driven by a bag;
a ventilator circuit where gas flow is driven by a bellows;
a flow diverter controllable to selectively open the bag circuit, open the ventilator circuit, and simultaneously open both the bag circuit and the ventilator circuit;
an inspiratory channel configured to transport inspiratory gases and an expiratory channel configured to transport expiratory gases;
a dry gas source connectable to the absorber outlet channel;
a controller configured to:
receive a user input to activate a drying mode; and
control a dry gas flow from the dry gas source to the absorber outlet channel and through the flow diverter to the bag circuit and the ventilator circuit so as to dry out moisture therefrom.

10. The system of claim 9, wherein the controller is further configured to open at least one valve to connect the dry gas source to an absorber outlet port.

11. The system of claim 9, wherein the controller is further configured to control at least one valve to connect the inspiratory channel to the expiratory channel.

12. The system of claim 9, wherein the $CO_2$ absorber is removable from the anesthesia breathing system and must be removed by a user prior to activation of the drying mode by the controller, wherein the absorber inlet channel includes an absorber inlet port with a valve that automatically closes when the $CO_2$ absorber is removed therefrom.

13. The system of claim 12, wherein the absorber outlet channel includes an absorber outlet port with a valve that automatically closes when the $CO_2$ absorber is removed therefrom.

14. The system of claim 9, wherein the dry gas source is an auxiliary $O_2$ supply of the anesthesia breathing system, and wherein the controller is configured to control a valve to connect the dry gas source to the absorber outlet channel.

15. A kit for drying an anesthesia breathing system, the kit comprising:
a switch retainer configured to be placed on a manually operable bag-to-vent switch lever of an anesthesia breathing system, wherein the switch retainer is configured to hold the bag-to-vent switch lever in an intermediate position between a bag position that closes a ventilator circuit and a ventilator position that closes a bag circuit; and
a dry gas input tube configured to connect an absorber outlet port of the anesthesia breathing system to a dry gas source such that dry gas flows through a ventilator channel and a bag channel simultaneously, the dry gas input tube having a $CO_2$ outlet fitting on one end that is configured to connect to the absorber outlet port when a $CO_2$ absorber is removed from the anesthesia breathing system and a dry gas source fitting on an opposite end of the dry gas input tube that is configured to connect to the dry gas source.

16. The kit of claim 15, further comprising an absorber inlet plug configured to block an absorber inlet port when the $CO_2$ absorber is removed from the anesthesia breathing system.

17. The kit of claim 16, wherein the absorber inlet plug is connected to the $CO_2$ outlet fitting.

18. The kit of claim 15, wherein the dry gas input tube is configured to connect the absorber outlet port to a wall gas supply.

19. The kit of claim 15, wherein the dry gas input tube is configured to connect the absorber outlet port to an auxiliary $O_2$ source of the anesthesia breathing system, and wherein the dry gas source fitting is configured to connect to an auxiliary $O_2$ port of the anesthesia breathing system.

20. The kit of claim 15, further comprising a short circuit connection tube configured to connect an inspiratory port to an expiratory port of the anesthesia breathing system.

* * * * *